(12) United States Patent
Brunner et al.

(10) Patent No.: US 7,633,676 B2
(45) Date of Patent: Dec. 15, 2009

(54) STEREOMICROSCOPE WITH COUPLING UNIT TO SWIVEL OBJECTIVE UPON SENSING MOVEMENT OF EYEPIECE

(75) Inventors: Robert Brunner, Jena (DE); Michael Haisch, Aalen (DE); Ulrich Naegele, Bartholomae (DE)

(73) Assignee: Carl Zeiss Jena GmbH, Jena (DE)

( * ) Notice: Subject to any disclaimer, the term of this patent is extended or adjusted under 35 U.S.C. 154(b) by 763 days.

(21) Appl. No.: 10/351,963

(22) Filed: Jan. 27, 2003

(65) Prior Publication Data
US 2004/0036962 A1  Feb. 26, 2004

(30) Foreign Application Priority Data
Jan. 28, 2002  (DE)  .................................. 102 03 215

(51) Int. Cl.
*G02B 21/22* (2006.01)
(52) U.S. Cl. .................. 359/369; 359/376; 359/384
(58) Field of Classification Search ................. 359/363, 359/368, 369, 376, 377, 378, 384; 348/51, 348/73, 74, 77, 79
See application file for complete search history.

(56) References Cited

U.S. PATENT DOCUMENTS

| 4,567,478 | A |   | 1/1986  | Schwab |
|-----------|---|---|---------|--------|
| 5,067,804 | A |   | 11/1991 | Kitajima et al. |
| 5,420,716 | A |   | 5/1995  | Fukaya |
| 5,545,120 | A | * | 8/1996  | Chen et al. ................. 600/117 |
| 5,825,532 | A | * | 10/1998 | Mochizuki et al. .......... 359/368 |
| 6,317,260 | B1| * | 11/2001 | Ito ............................. 359/377 |
| 6,525,878 | B1| * | 2/2003  | Takahashi ................... 359/466 |
| 6,661,571 | B1| * | 12/2003 | Shioda et al. ............... 359/372 |

FOREIGN PATENT DOCUMENTS

DE  4 321 934  *  1/1994
EP  0 088 985  *  9/1983

* cited by examiner

*Primary Examiner*—Alessandro Amari
*Assistant Examiner*—Mark Consilvio
(74) *Attorney, Agent, or Firm*—Patterson, Thuente, Skaar & Christensen, P.A.

(57) ABSTRACT

In a microscope comprising an objective and an eyepiece, which displays images of an object sensed by the objective, as well as comprising a camera which records the images of the object sensed by the objective, an eyepiece is provided which senses an image generated by a display, said display displaying the image recorded by the camera.

13 Claims, 6 Drawing Sheets

STEREOMICROSCOPE WITH COUPLING UNIT TO SWIVEL OBJECTIVE UPON SENSING MOVEMENT OF EYEPIECE

The invention relates to a microscope comprising an objective and an eyepiece, said microscope displaying images of an object sensed by said objective, as well as a camera which records images of the object sensed by said objective.

The image-enlarging properties of microscopes are often employed to assist micromechanical manipulations, in order to perform high-precision surgical operations on the smallest scale, as required, for example, in vascular surgery. This makes enlargement of the image of the field of activity, e.g. of an operating field, indispensable. Conventional surgical microscopes, as disclosed, for example, in U.S. Pat. No. 5,383,637, are usually structured such that the object field to be viewed is presented to the surgeon by an objective turning the object field into an intermediate image which is then presented to the eye by means of an eyepiece. To allow viewing of the desired object field, the objective must be placed very precisely at a defined location, thus automatically defining the posture of the surgeon as well. However, as a result, a very unfavourable and uncomfortable working posture may have to be assumed, so that such manipulatory or surgical microscopes are often considered to be ergonomically disadvantageous.

In order to overcome these ergonomic disadvantages, it is known, for example, from U.S. Pat. No. 5,867,210, to provide a surgical microscope with a camera and to transmit the image thus recorded to a monitor. Although such monitors may be mounted on special supporting arms, as known, for example, from U.S. Pat. No. 6,317,260, they can be arranged in space, in particular in operating theaters, only to a limited extent, so that, in this case, the surgeon's freedom of movement is also unfavourably affected. Moreover, in connection with such microscopes, surgeons often complain that the optical control of manual activities in such a monitor image is very tiresome.

Therefore, it is an object of the invention to provide a microscope which avoids the ergonomic disadvantages of the prior art.

According to the invention, this object is achieved by a microscope of the above-mentioned type in that the eyepiece senses an image generated by a display, said display displaying the image recorded by the camera.

Thus, the invention overcomes the ergonomic disadvantages of the prior art by separating the positions of the objective and of the eyepiece. The microscope is divided into a recording unit and a display unit, which can be independently moved relative to each other. The eyepiece no longer inevitably senses an intermediate image generated by the objective, but instead senses an image generated in a display which is fed by a camera. By separating the optical path from the objective to the eyepiece, the compulsory postures of a user of such microscope, which have been considered as unergonomic, are no longer required. The eyepiece can now be arranged in a freely selectable manner relative to the objective. Nevertheless, the fixed position of the head during use of the microscope as desired by users is possible because the surgeon rests his head against the eyepiece. However, the position of the head can now be adjusted and is not stringently determined by the microscope.

Thus, the microscope according to the invention assists micromechanical manipulations, in particular in surgery, by establishing a fixed reference, for the very precise, fine and complex operations to be carried out, relative to the object on which said manipulations are carried out. This is ensured by the invention in that the surgeon rests his head against the eyepiece of the microscope during the operation. This mechanical-sensory perception allows the surgeon to control his position relative to the microscope. Since the microscope is fixed relative to the patient, the surgeon also has a fixed reference to the patient and, thus, to the field of operation. Thus, said optical control is effectively assisted by the mechanical-sensory feedback between the contact of the head and manual activity.

In microscopes, in particular in surgical microscopes, the objective and the camera are usually mounted on a common microscope stand to ensure that these two components are locked in position relative to each other, as required. In surgical microscopes, the microscope stand is usually adjustable along at least two axes. In order to achieve free adjustability and fixability of the eyepiece in a selected position, use is conveniently made of an independent eyepiece stand carrying said eyepiece. It has turned out as favourable in such embodiments if the eyepiece stand is attached to the microscope and is freely adjustable relative to said microcscope, since the microscope then constitutes one single device. Moreover, a wire data connection between the camera and the display may be laid out in a manner particularly safe from interference, without the stringent requirement of complicated plug connections.

In order to allow a user to find the desired fixed position of the head during use of the microscope, i.e. to allow the eyepiece to be arranged in a selectable, but then fixable spatial position, it is advantageous to mount the eyepiece on an eyepiece stand which is adjustable relative to the objective. Such eyepiece stand then allows unrestricted positioning relative to the microscoped object, for example, a patient. The separation of the objective and of the eyepiece allows the optical access to the object field to be freely positioned and, at the same time, to select the most suitable and most comfortable working posture. Advantageously, the eyepiece can be adjustably fixed in a spatially fixed and stable manner, for example, via screws or via magnetic brakes in the joints. In the case of smaller stands, friction can be employed as well, i.e. attachment means are tightened so strongly that the stand will not shift automatically, but can be newly positioned by urging/pushing/pulling. Springs or hydraulic cylinders additionally allow to achieve a weight balance. In an advantageous embodiment, the joints of the stand are of such easy action that the stand can be repositioned via a nose support or a mouthpiece, since a surgeon will then not have to lay down his surgical instruments. It is then possible that a surgeon may find an adjustable, stable contact for his head and may thus work on the patient in a stable manner.

In order to avoid transmission of undesired vibrations from the eyepiece, against which the surgeon rests his head, to the microscope, it is advantageous to provide an eyepiece stand attached to a microscope stand with a vibration decoupling device, e.g. as a mechanical low-pass filter.

A particularly ergonomic design is obtained by using a stereoscopic camera and a stereoscopic eyepiece which senses stereoscopic images generated by the display. Said eyepiece can then be provided as a known binocular element which senses images from a suitable, stereoscopic display.

For long-time use of a microscope, it may often be convenient, for ergonomic reasons, if a person using the microscope can alter their posture. Further, depending on the application, it can also be required to approach the object field in a different manner, for example, at a different angle or from a different direction. In such cases, it is advantageous to provide a coupling unit which senses a movement of the eyepiece and accordingly moves the objective and/or the camera. For example, if a surgeon wishes to rotate the image represented in the eyepiece about 90°, he can just turn the eyepiece around 90°.

The coupling device then accordingly turns the camera/objective unit. In doing so, both the objective and the camera can be moved, and the camera can also be turned alone. This may be preadjusted in an application-dependent manner or may be selectable. If a user of a microscope, however, only wishes to shift the predetermined posture of his head without effecting a change in the field of view in the microscope, it is convenient that the coupling device be provided such that it may be switched off in order to allow a surgeon to switch off the coupling device and then guide the eyepiece into a new position.

The coupling device may be of a mechanical type, for example, a suitable linkage between the eyepiece and the objective/camera. This is realized in a particularly easy manner by a rotary sensor on the eyepiece and a rotary drive on a microscope stand carrying the objective. Coupling is then effected in an electromechanical manner, with the rotary sensor, which is preferably a three-axial sensor, sensing a rotation of the eyepiece and the rotary drive accordingly adjusting the objective/camera. Such electromechanical coupling is not only particularly easy to switch off, but it also allows a freely selectable transmission/reduction ratio, which may be adapted, in particular, to the magnification of the microscope. A suitable control unit for the microscope is conveniently provided, which control unit effects coupling as a function of the microscope magnification. Said coupling allows a larger image field to be used, because a user of the microscope can virtually "look around" within the object field by suitably rotating the eyepiece.

In most operations, the optical axis of the microscope is perpendicular to the operating table or is slightly inclined to the vertical plane. The surgeon essentially moves only along a circular path around the operating field, which he must always be able to reach with his hands, of course. In this respect, it is ergonomically favourable, if the microscope and the eyepiece are fixed to a rotary shaft, in particular a vertical rotary shaft, which intersects the object field near the focal point or in the focal point. The eyepiece stand is advantageously embodied such that the rotary shaft coincides with the optical axis of the microscope.

The use of a display in the eyepiece not only allows the images provided by the camera to be displayed in the eyepiece, but also allows to display further information which is not, or not directly, obtained from microscope camera images. Said information may be additional information in the sense of a surgical navigation, wherein individual structures detected in the image recorded by the camera are specially highlighted or combined with other information, such as information derived from X-ray images or from computer-tomographical images. In most cases, surgical microscopes are provided with a small screen on the stand, which screen assists control of the microscope. The information on said screen could now (also) be displayed in the eyepiece. Furthermore, there is an increasing desire for digital recording of moving images or of still images. These images can also be displayed in the eyepiece, e.g. in order to allow another look at an earlier state of the operation. Further, the use of a display enables free arrangement of the information in the visual field which is viewed through the eyepiece. In this connection, use may be made of the windows technique known from computer displays.

The images recorded by the camera may be transmitted to the display in manifold ways. For example, wireless transmission or multiple-fiber light guide cable bundles may be conceived of. However, surgical microscopes, in particular, require a high image quality in combination with as little interference as possible being caused to other instruments usually present in an operating theater. For such applications, a wire data connection is convenient via which the image data of the images recorded by the camera are transmitted between the camera and the display.

The display which generates said images, which are sensed by the eyepiece, may be realized in manifold ways. Use may be made of nearly all conventional principles of electronic projection. For example, an autostereoscopic displaying system may be used. LCD displays are a particularly simple embodiment. However, they require a light source for generating images. For this purpose, a particularly convenient embodiment uses a light source which is already present for operation of the microscope. Therefore, advantageously, a light source is associated with the objective, the display comprises an LCD display, and a light guide is provided which guides light generated by said light source to the LCD display. This obviates the need for an additional light source for operation of the LCD display. Depending on the design of the LCD display, the light coupled out from the light source associated with said objective may be guided to the LCD eyepiece either as white light or as tricolor RGB light. In a microscope whose objective operates on white light, which is usually the case in surgical microscopes, a tricolor wheel, rotated in the optical path, may be used to generate said RGB light.

In surgical operations, there is usually a surgeon and an assistant, both of whom advantageously see the image generated by the microscope. Therefore, a microscope system according to the invention will advantageously have at least two eyepieces.

During some operations, the surgeon and his assistant stand next to each other or also at 90° to each other. In this case, a microscope is advantageous which can generate pairs of stereoscopic images with a correct stereoscopic basis for both viewers. In such a microscope, both eyepiece stands are preferably freely movable relative to each other, e.g. about a common axis, and communicate their position to a microscope control system via a rotary sensor and a data line.

In other operations (e.g. spinal column operations), the patient lies in the middle between the surgeon and his assistant. The microscope is then located vertically above the patient. In this case, both eyepieces are preferably positioned at 180° (+/−20°) relative to each other. One eyepiece directly displays, the right way around, the pair of stereoscopic images produced by the cameras. In the other eyepiece, said images are "upside down", and the image of the right-hand camera is displayed in the left-hand eyepiece, and vice versa. Thus, said eyepieces preferably show images having a stereoscopic basis which corresponds to the spatial position of the eyepieces relative to the object field, e.g. relative to the focal point.

Optionally, a small operating panel may be mounted next to the eyepiece, allowing control of movements of the stand, of microscope and illumination settings or of other devices. In classic surgical microscopes, such an operating part is located on the handle, by means of which the position of the microscope is correctly adjusted, allowing, for example, actuation of a photographic camera or of a video recorder, fading-in of an endoscopic image, control of lighting intensity or a surgical navigation.

The microscope according to the invention allows a particularly ergonomic use as a surgical microscope, since a surgeon, while being able to freely select the posture of the head relative to the objective, may also fix said posture during the operation. Therefore, the use of the microscope according to the invention as a surgical microscope is particularly preferable. A typical and comfortable inclination of the viewing direction to the horizontal plane is, for example, 15°. The distance between the objective and the focal point is preferably at 250 to 400 nm, but the distance between the focal point and the surface of the body may well be 100 mm. The vertical distance between the focal point and the eye is typically 500 to 600 nm, the horizontal distance is usually 250 to 350 mm. These values are values obtained by experience. In principle, they vary quite strongly according to the height of the surgeon and the operating technique used. In this connection, the microscope according to the invention allows optimal adjustment. In operations on the brain or on the ear, nose or throat, said distances may have other values. In particular, it is also possible that the optical axis is nearly horizontal, in which case the distances remain approximately the same.

The invention will be explained in more detail below, by way of example and with reference to the Figures, wherein.

Figure 1:
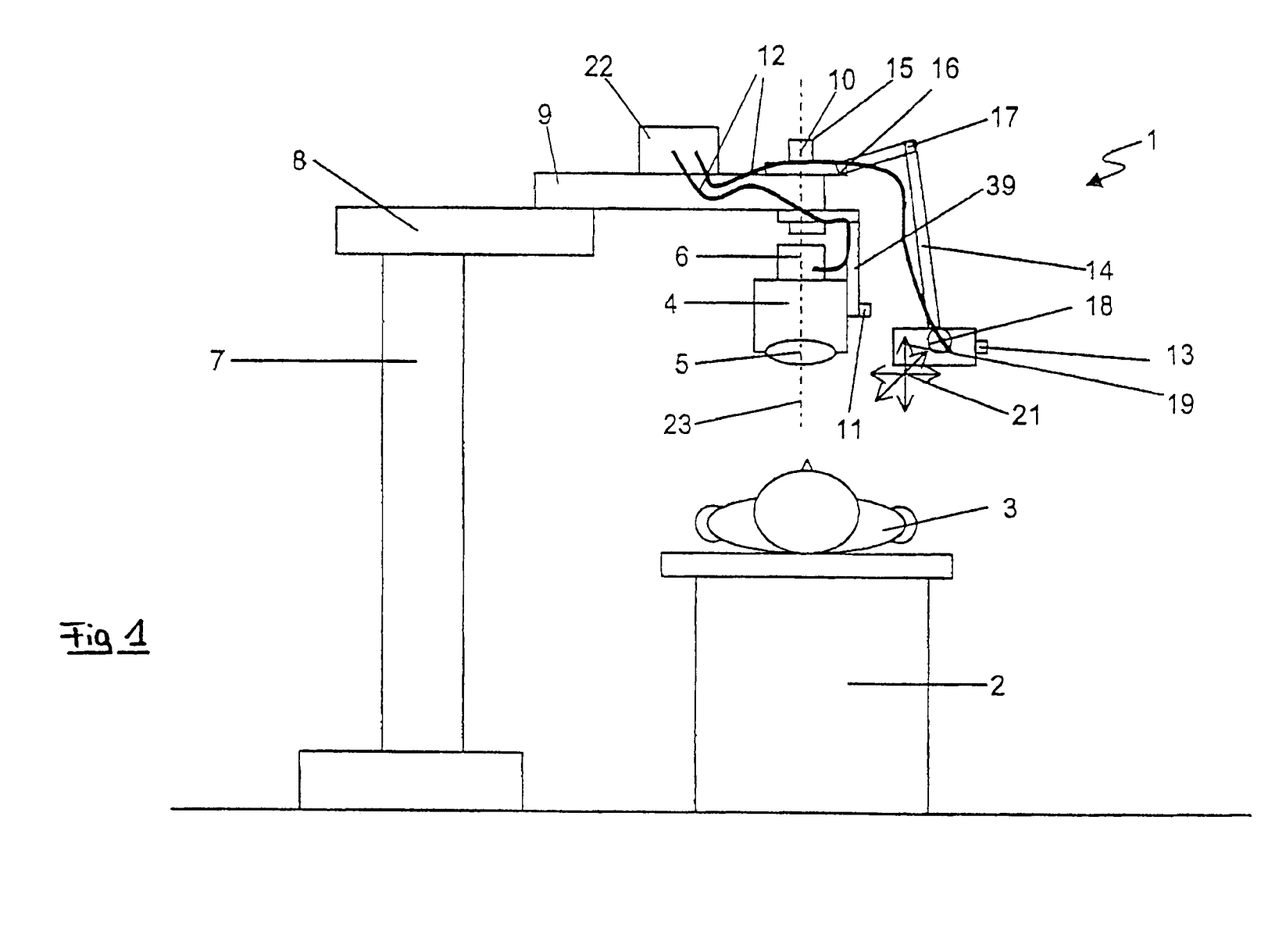
FIG. 1 shows a schematic view of a surgical microscope.

FIG. 1 schematically shows a surgical microscope 1, which is mounted next to an operating table 2. A patient 3 lies on the operating table 2 during an operation. The operating field is sensed by an incident-light microscope 4 which comprises an objective 5 as well as a camera 6. In doing so, the objective 5 senses the operating field and the camera 6 is arranged following the objective 5 in the beam path, so as to generate an enlarged image of the operating field. A suitable incident-light microscope is offered, for example, by Carl Zeiss, Oberkochen, Germany, and is designated as OPMI Vario. A stereoscopic camera was added to it.

The incident-light microscope 4 is mounted to a microscope stand 7, which allows, via rotary joints 8 to 11 and a bracket 39, multi-axial adjustment of the incident-light microscope 4, so that the latter may be displaced above the operating table 2 almost at will. In doing so, the optical axis 23 is perpendicular to the operating table 2 in the design as shown.

The camera 6 records images showing the object field sensed by the objective 5. Said camera is provided as a pair of stereoscopic cameras and delivers its stereoscopic images to an electronic eyepiece 13 via a data line 12. Said eyepiece 13 is a conventional microscopy eyepiece which is adapted for resting one's head against it and has an LCD display 19 arranged in its intermediate image plane. Since said eyepiece is a stereoscopic eyepiece 13, there are accordingly provided, for said pair of cameras, two displays 19 as well as a device for adjusting the pupil distance and a device for correcting defective vision. In the following, only one display 19 is mentioned for simplification.

The LCD display 19 is connected to the data line 12 and shows corresponding stereoscopic images which a surgeon may view in the stereoscopic eyepiece 13. The eyepiece 13 is mounted on an eyepiece stand 14, which is in turn mounted to the microscope stand 7. The eyepiece stand 14 comprises rotary joints 15 to 18, which allow freely selectable, triaxial positioning of the eyepiece 13 in space and, in particular, relative to the incident-light microscope 4. This is symbolized by arrows 21 in FIG. 1. The eyepiece stand 14 is provided such that the selected position can be fixed by accordingly fixing the rotary joints 15 to 18.

A control unit 22 is mounted to the microscope stand 7, said control unit 22 being connected to the data line 12 which connects the eyepiece 13 with the camera 6. The rotary joints 15 to 18 are provided with rotary sensors which are connected with the control unit 22 via the data line 12. The control unit 22 thus senses a rotation of the eyepiece 13. The incident-light microscope 4 is provided with a rotary drive which rotates the camera 6 relative to the objective 5. Said rotary drive is suitably controlled by the control unit 22, so that a corresponding rotation of the eyepiece 13, which the control unit 22 senses via the rotary sensors, is converted into a corresponding movement of the rotary drive and, thus, into a corresponding rotation of the camera 6.

If a surgeon, resting his head against the eyepiece, rotates or displaces the eyepiece 13 when the control unit 22 is operative, the image displayed on the LCD display 19 in the eyepiece 13 changes to the same extent, but in the opposite direction, because the camera 6 is accordingly rotated. Thus, the surgeon has the impression of a spatially fixed image.

According to a further embodiment, the rotary drive is not provided for rotation of the camera 6, but effects a corresponding movement of the entire incident-light microscope 4, such that any movement of the eyepiece 13 in the direction of the arrows 21 or a corresponding rotation results in a corresponding movement or rotation of the incident-light microscope 4, when the control unit 22 is operative. Thus, the surgeon can "look around" in a larger image field using his eyepiece, since an eyepiece movement is immediately converted into a corresponding movement of the incident-light microscope 4.

Alternatively, an electronic image-field adjustment may also be effected as follows. In this embodiment, the LCD display 19 shows only a partial segment of the image provided by the camera 6. If the control unit 22 detects a rotation of the eyepiece 13, the image field segment displayed in the LCD display 19 is accordingly displaced so that, by rotating the eyepiece 13, the viewer can "look around" in the entire image provided by the camera 6.

In further embodiments of the surgical microscope 1, the eyepiece stand 14 is not mounted on the microscope stand 7. Instead, according to one embodiment, it is separately fixed to the floor and, according to another embodiment, it is separately fixed to the ceiling.

For operation, the LCD display 19 requires a light source. For this purpose, light is coupled out, via a light-wave guide 12a from a light source (not shown), which is present on the incident-light microscope 4 anyway, and said light is transmitted to the LCD display 19 in parallel with the data line 12. The light source on the incident-light microscope 4 provides white light. For LCD displays requiring tricolor RGB light, a color wheel is placed in the beam path from the light source of the incident-light microscope 4 to the LCD display 19, said color wheel generating the suitable RGB light for the LCD display 19 upon corresponding passage through colored sectors.

Figure 2:
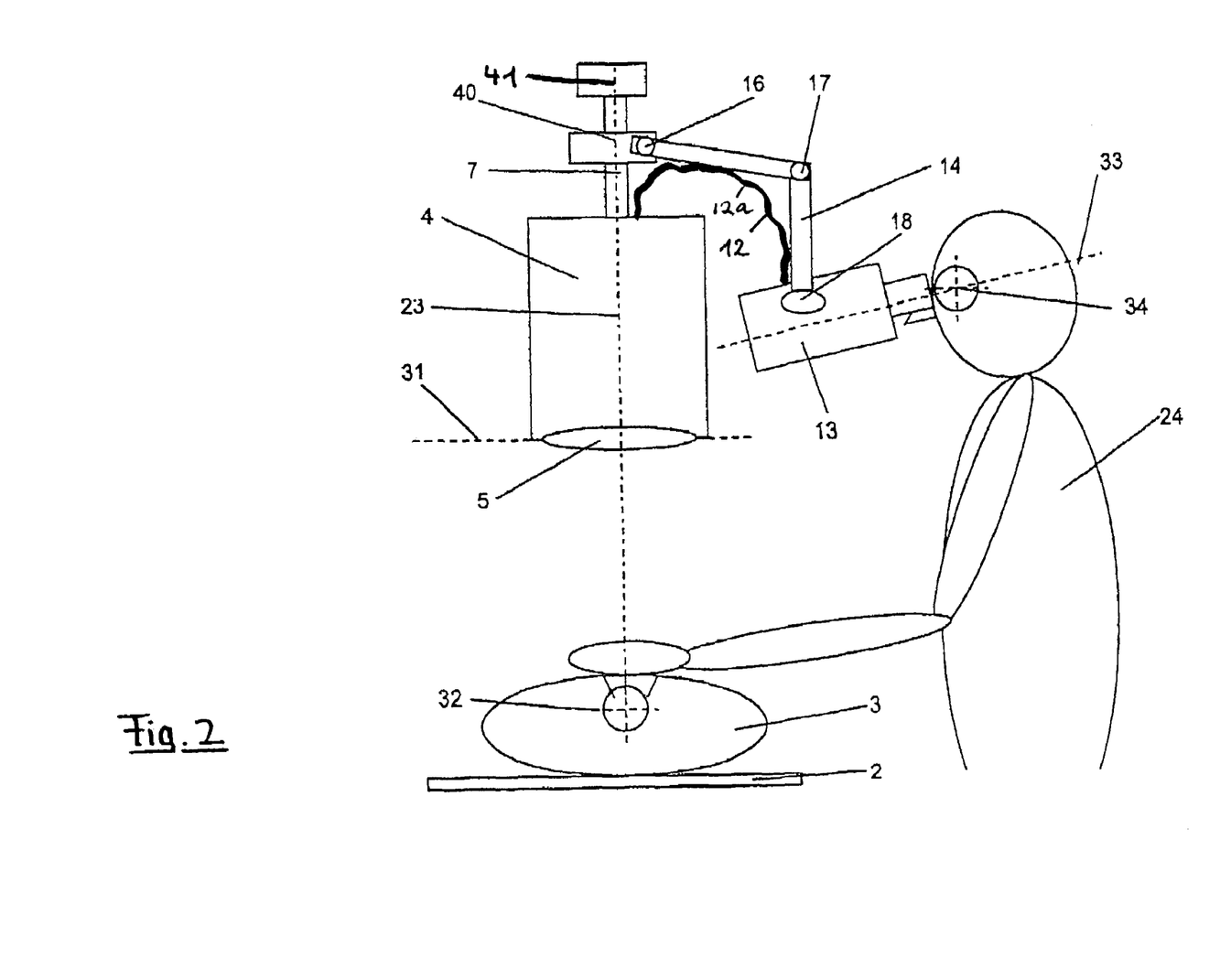
FIG. 2 shows a schematic view of a surgical microscope comprising an eyepiece stand and a microscope stand which are arranged parallel to each other.

Depending on the field of application, e.g. depending on the type of operation, the mechanical separation of the eyepiece 13 and of the incident-light microscope 4 allows to realize the most favourable ergonomic setup. FIG. 2 shows an advantageous arrangement for spinal column surgery, which is a typical example of an operation in which a surgeon 24 moves essentially along a circular path around the operating field, so that he can always reach it with his hands. For such applications, the optical axis 23 of the incident-light microscope 4 is conveniently perpendicular to the operating table 2 on which the patient 3 lies. Upon rotation of the microscope 4 on its microscope stand 7, the focal point 32 on the patient 3 does not change. Moreover, the distance between an objective plane 31 of the objective 5 and the plane of the focal point 3 remains unchanged.

Figure 3:
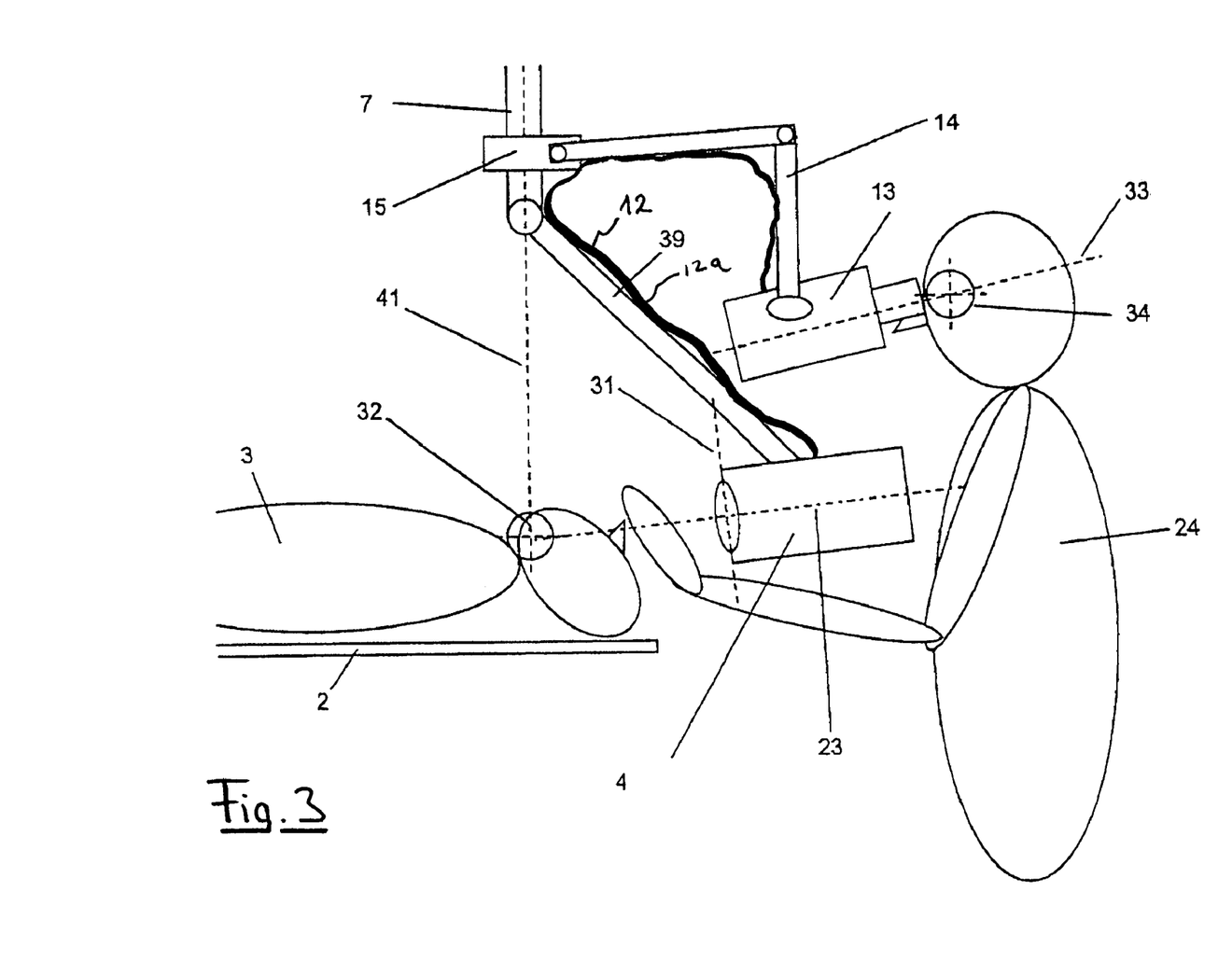
FIG. 3 shows a schematic view of a surgical microscope having a near-horizontal optical axis.

In this case, a particularly convenient ergonomic arrangement is achieved if it allows a surgeon 24 to maintain his viewing direction 33 while moving around the operating field. Since this requires his eye position 34 relative to the eyepiece 13 to remain unchanged, the eyepiece stand 14 is advantageously guided in parallel with the optical axis 23 in such applications. Therefore, in the embodiment of FIG. 2, the microscope stand 7 and the eyepiece stand 14 are provided on a common axis of rotation 41 which intersects the focal point 32. In FIG. 2, the axis of rotation 41 coincides with the optical axis 23. However, as FIG. 3 shows, this is not mandatory.

In order to achieve vibration-decoupling between the eyepiece 13 and the microscope 4, the eyepiece stand 14 is mounted to the rotary shaft 41 via a vibration damper 40.

An ergonomically comfortable inclination of the viewing direction 33 to the horizontal plane is in the order of magnitude of 15°. The distance between the objective plane 31 and the focal point 32 is regularly between 25 and 40 cm, but the distance between the focal point 32 and the surface of the body of the patient 3 may well be 10 cm. Depending on the physique of the surgeon 24, the vertical distance between the focal point and the eye is between 50 and 60 cm, so that the surgeon 24 may easily reach the operating field on the patient 3. The horizontal distance is then usually between 25 and 35 mm. However, these values may also vary according to the height of the surgeon 24 and according to the operating technique used.

In the embodiment of FIG. 2, the partly parallel course of the microscope stand 7 and the eyepiece stand 14 allows easy adjustment to the surgeon's needs. In particular, the surgeon may adjust the height of the eyepiece by means of the two joints 16 and 17 in the eyepiece stand 14, while maintaining the same inclination.

Another geometry of an incident-light microscope 4 and of an eyepiece 13 is shown in FIG. 3, which relates to a surgical operation on the brain or on the ear, nose or throat. There, the distances may also assume other values; in particular, the vertical distance between the eye position 34 and the focal point 32 may be substantially lower, in some cases it may even be negative. As can be seen, the optical axis 23 of the incident-light microscope 4 is nearly parallel to the plane of the operating table 2 or assumes a very acute angle relative thereto. In spite of this arrangement, the viewing direction 33 of the surgeon 24 is adjustable to the ergonomically favourable value of about 15°. As shown in FIG. 3, the microscope stand 7 and the eyepiece stand 14 are, in this case, also fixed to a common rotary shaft 41, so that the surgeon 24 may effect a circular movement around the operating field also in this case.

Figure 4:
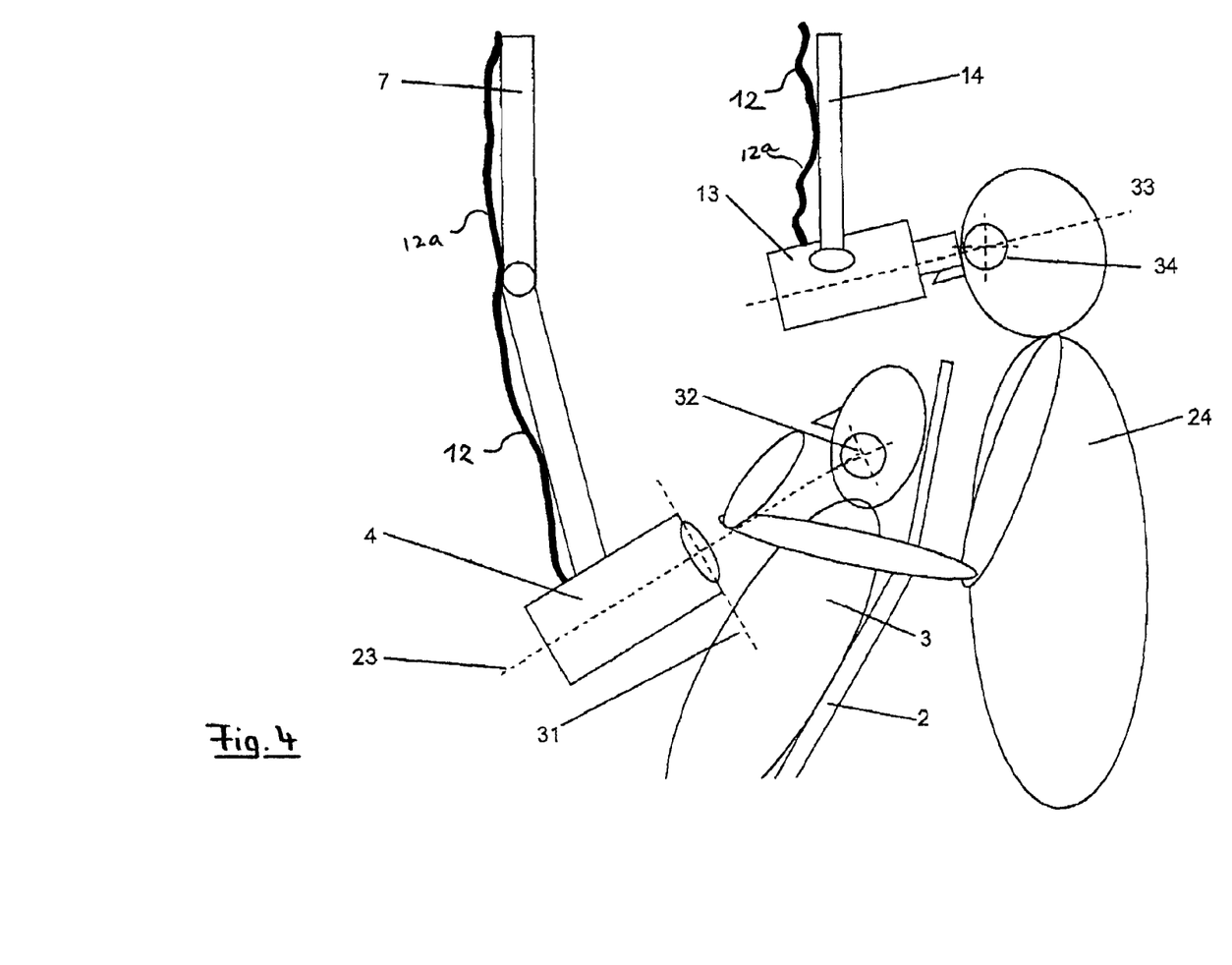
FIG. 4 shows a schematic view of a surgical microscope for dental surgery.

The great freedom achieved by separating the eyepiece 13 and the incident-light microscope 4, is shown, quite impressively, in FIG. 4. In this case, the optical axis 32 extends in an obliquely upward direction, so as to allow the surgeon 24 an optimal view in dental surgery or during surgery on the upper jaw.

Figure 5:
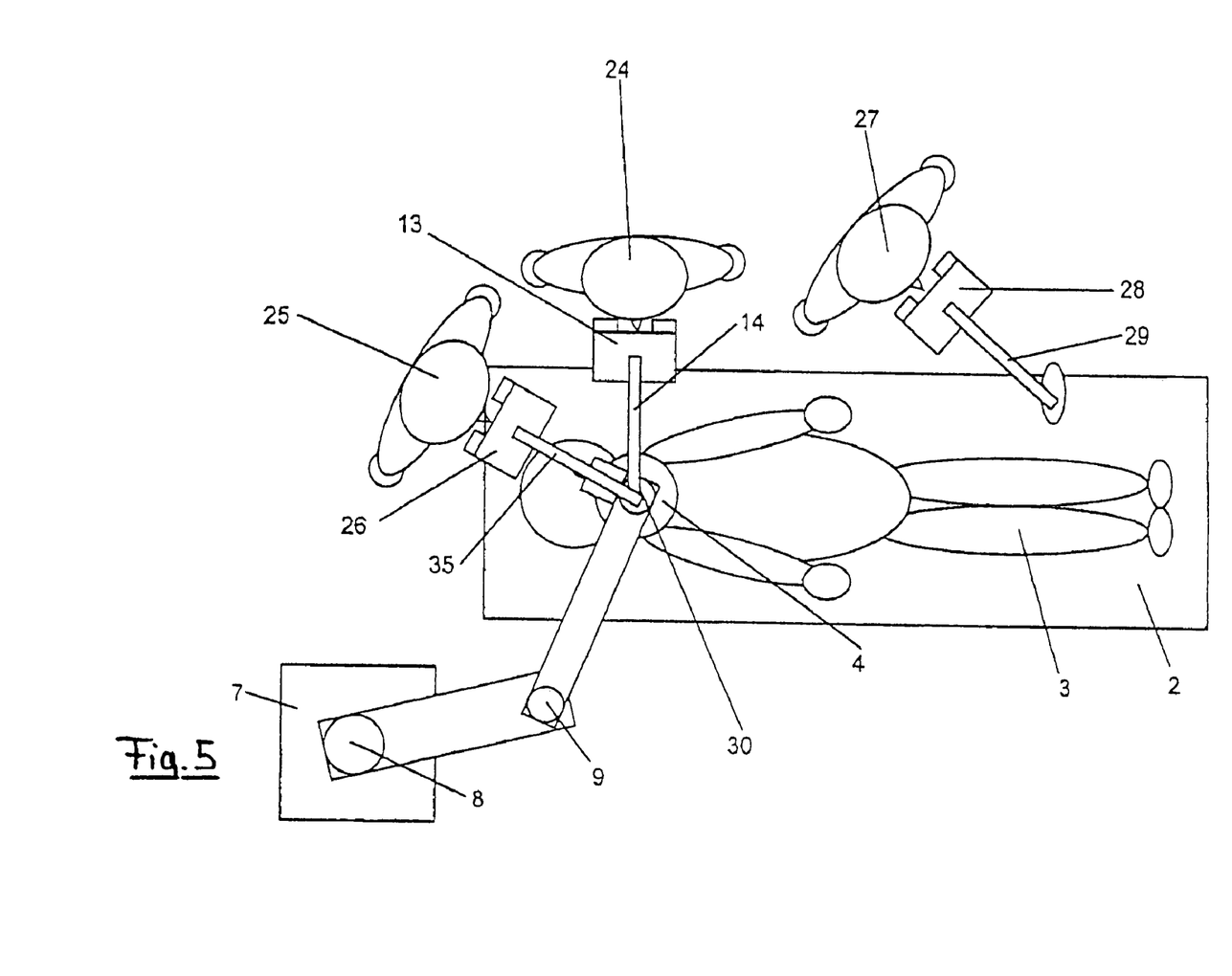
FIG. 5 shows a schematic view of a surgical microscope comprising three eyepieces.

However, not only does the large mechanical separation of the eyepiece 13 and of the incident-light microscope 4 provide maximum freedom in the arrangement of the incident-light microscope and of the eyepiece relative to each other, but it also allows easy replication of the images of the operation. FIG. 5 shows a corresponding arrangement wherein, similar to FIG. 1, the optical axis is perpendicular to the operating table 2. In addition to the microscope stand 14 with eyepiece 13 for the surgeon 24, a further unit is provided, in this case, for an assistant 25, who also has his own eyepiece 26, which is mounted on a second eyepiece stand 35. The eyepiece stand 14 and the second eyepiece stand 35 are connected with each other via the aforementioned rotary sensor so that the position of the eyepiece 13 and of the second eyepiece 26 relative to each other may be kept constant even when the camera 4 is moved by the control unit 22. Further, the angle of the eyepieces to a given direction may be measured so as to control the microscope.

Moreover, according to the embodiment of FIG. 5, a third eyepiece 28 for a surgical nurse 27 is provided and fixed to the operating table 2 by means of a table stand 29. The look into the third eyepiece 28 allows the surgical nurse 27 to recognize early which instruments need to be passed to the surgeon 24 or to the assistant 25.

Figure 6:
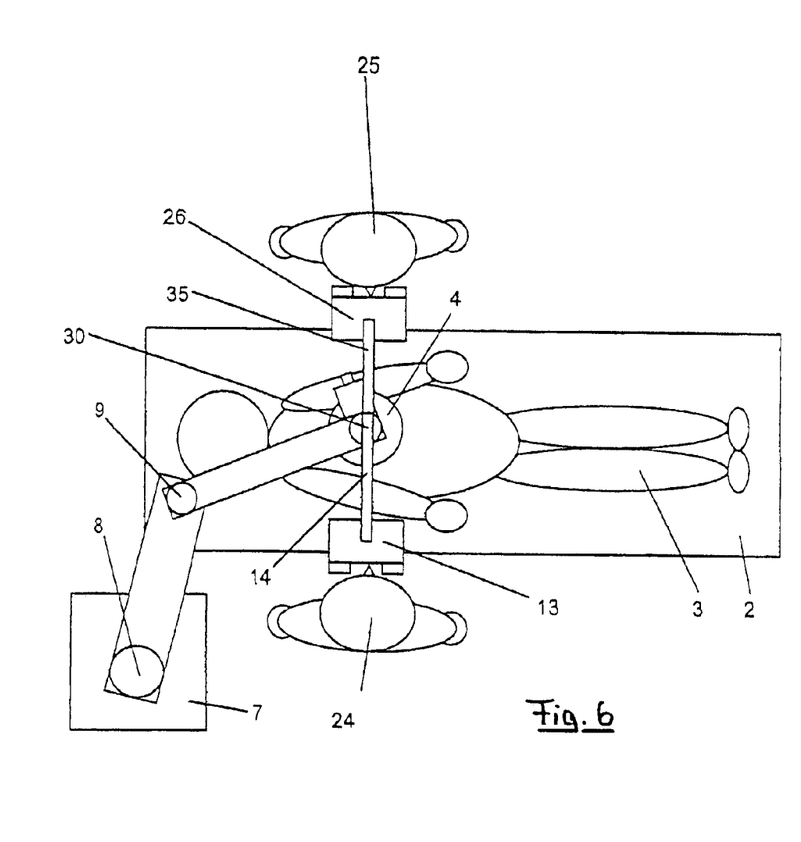
FIG. 6 shows a surgical microscope similar to that of FIG. 5, but with opposing eyepieces.
Figure 7:
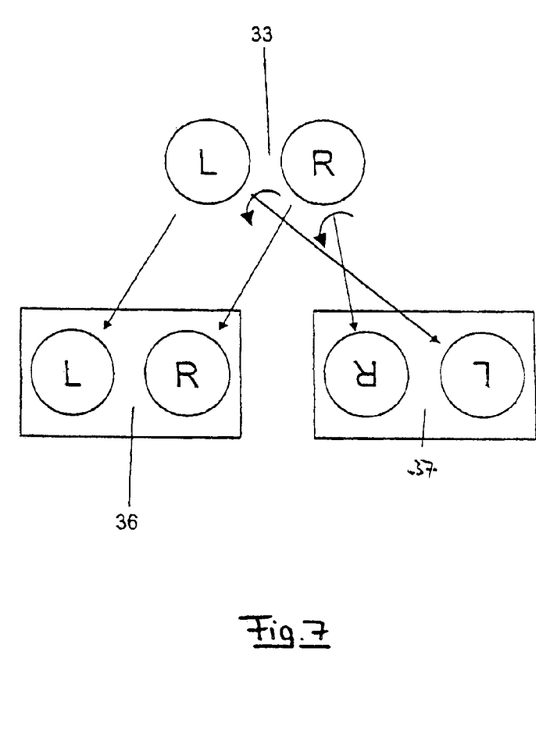
FIG. 7 shows a schematic view of image correction in the microscope of FIG. 6.

However, the rotary sensor 30 in the embodiment of FIG. 5 serves not only to adjust the position of the eyepiece 13 and of the second eyepiece 26 relative to each other in the case of movements of the incident-light microscope 4, but it may also be evaluated for image correction if an operating arrangement as shown in FIG. 6 is present. In this case, the eyepiece 13 and the second eyepiece 26 are directly opposite each other. The eyepiece 13 of the surgeon 24 shows an eyepiece view 36 which is represented in FIG. 7. The pair of stereoscopic images 38 is the right way around in the eyepiece view 36 and is not inverted. The second eyepiece view 37 is inverted and mirrored to allow the assistant 26 to also see an image in the second eyepiece 26 which is related to his standing-point opposite the surgeon 24. Thus, both eyepieces show the respective images having a stereoscopic basis which corresponds to the spatial position of the eyepieces relative to the object field or to the operating field. The required image inversion is caused by the control unit 22 by reflecting the pair of stereoscopic images, point by point, as soon as the control unit 22 realizes, on the basis of the read-out of the rotary sensor 30, that the second eyepiece 26 is opposite, or nearly opposite, the eyepiece 13 (e.g. 180°+/−20°).

In a further embodiment which corresponds essentially to that of FIG. 1, a so-called x/y-coupling is realized. Said x/y-coupling allows, via adjustment of the microscope attachment to the bracket 39 and to the rotary joint 10, a displacement of the microscope 4 perpendicular to the optical axis 23. In order to enable easy movement of the eyepiece 13, the eyepiece stand 14, in this case, is not attached to a point lying on the optical axis 23, but to another point on the microscope stand 7, e.g. to the joint 8 or 9. In this manner, the eyepiece 13 may optionally, but not necessarily, also move along during said displacement.

The invention claimed is:
1. A microscope comprising:
an objective,
a camera that records images of an object sensed by the objective, the camera being operably coupled to the objective,
a display displaying the images recorded by the camera and at least one eyepiece, that senses the images generated by the display, and that comprises a binocular element, which has an intermediate image plane, the display being located in the intermediate image plane; and wherein the microscope further comprises a coupling unit, that can be switched off, said coupling unit sensing a movement of the eyepiece, and accordingly moving the objective to swivel or shift its viewing axis.

2. The microscope as claimed in claim 1, characterized in that the eyepiece comprises a head rest and is mounted on an eyepiece stand which is adjustable relative to the objective.

3. The microscope as claimed in claim 2, characterized in that the eyepiece stand is mounted on a microscope stand carrying the objective and the camera.

4. The microscope as claimed in claim 1, further comprising a control device which can be switched between an operative status in which a movement of the eyepiece results in a corresponding movement of the camera and an inoperative status in which the eyepiece can be positioned relative to the object without the camera being moved.

5. The microscope as claimed in claim 4, characterized by further comprising a rotary sensor on the eyepiece stand and by a rotary drive on a microscope stand carrying the objective.

6. The microscope as claimed in claim 1, wherein the display also displays additional information which is not obtained from the camera.

7. The microscope as claimed claim 1, further comprising a data line between the camera and the display, which data line is provided for transmission of image data of the images recorded by the camera.

8. The microscope as claimed in claim 1, further comprising a light source for illuminating the object is associated with the objective, and wherein the display comprises an LCD display, and a light guide is for guiding light generated by said light source to the LCD display.

9. The microscope as claimed in claim 1, characterized by a stereoscopic camera and a stereoscopic eyepiece which senses stereoscopic images generated by the display.

10. The microscope as claimed in claim 1, further comprising an additional eyepiece.

11. The microscope as claimed in claim 10, further comprising a control unit which, in both eyepieces generates stereoscopic images having a stereoscopic basis corresponding to the respective spatial position of the eyepieces relative to the object field.

12. The microscope as claimed in claim 10, wherein the eyepieces are moveable independently of each other.

13. The microscope as claimed in claim 1, for use as a surgical microscope.

* * * * *